United States Patent
Anderle et al.

(10) Patent No.: US 11,291,823 B2
(45) Date of Patent: Apr. 5, 2022

(54) COUPLING COMPONENT AND FLUID COUPLING

(71) Applicant: FRESENIUS MEDICAL CARE DEUTSCHLAND GMBH, Bad Homburg (DE)

(72) Inventors: Jens Anderle, Deggingen (DE); Hannes Wirtl, Schongau (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 406 days.

(21) Appl. No.: 16/470,563

(22) PCT Filed: Dec. 17, 2017

(86) PCT No.: PCT/EP2017/083183
§ 371 (c)(1),
(2) Date: Jun. 18, 2019

(87) PCT Pub. No.: WO2018/114726
PCT Pub. Date: Jun. 28, 2018

(65) Prior Publication Data
US 2019/0344067 A1 Nov. 14, 2019

(30) Foreign Application Priority Data
Dec. 21, 2016 (DE) ...................... 10 2016 015 205.2

(51) Int. Cl.
*A61M 39/26* (2006.01)
*A61M 39/06* (2006.01)
(Continued)

(52) U.S. Cl.
CPC ............ *A61M 39/26* (2013.01); *A61M 39/06* (2013.01); *A61M 39/10* (2013.01);
(Continued)

(58) Field of Classification Search
CPC ...... A61M 39/26; A61M 39/06; A61M 39/10; A61M 2039/0072; A61M 2039/064; A61M 2039/2426; F16L 37/38; F16L 2201/40
See application file for complete search history.

(56) References Cited

U.S. PATENT DOCUMENTS

| 5,064,416 A | 11/1991 | Newgard et al. |
| 8,100,869 B2 | 1/2012 | Vangsness et al. |

(Continued)

FOREIGN PATENT DOCUMENTS

WO 2009137396 A1 11/2009

OTHER PUBLICATIONS

International Preliminary Report on Patentability issued in corresponding International Patent Application No. PCT/EP2017/083183 dated Jun. 25, 2019 (8 pages).
International Search Report and Written Opinion issued in corresponding International Patent Application No. PCT/EP2017/083183 (with English translation of International Search Report) dated Mar. 27, 2018 (11 pages).

*Primary Examiner* — Lauren P Farrar
(74) *Attorney, Agent, or Firm* — Kilyk & Bowersox, P.L.L.C.

(57) ABSTRACT

The invention relates to a coupling component for a fluid coupling (1) for releasably connecting fluid-conveying components, in particular fluid-conveying components in medical equipment, wherein the coupling component comprises a coupling housing (14) through which a fluid channel (17) passes in regions and which is provided with a coupling recess (7) that is sunken into a surface (15) of the coupling housing (14), wherein a channel opening (18) of the fluid channel (17) ends at an end face (19) of the coupling recess (7). According to the invention, it is provided that the channel opening (18) is covered by a membrane seal (4)

(Continued)

Figure 1:
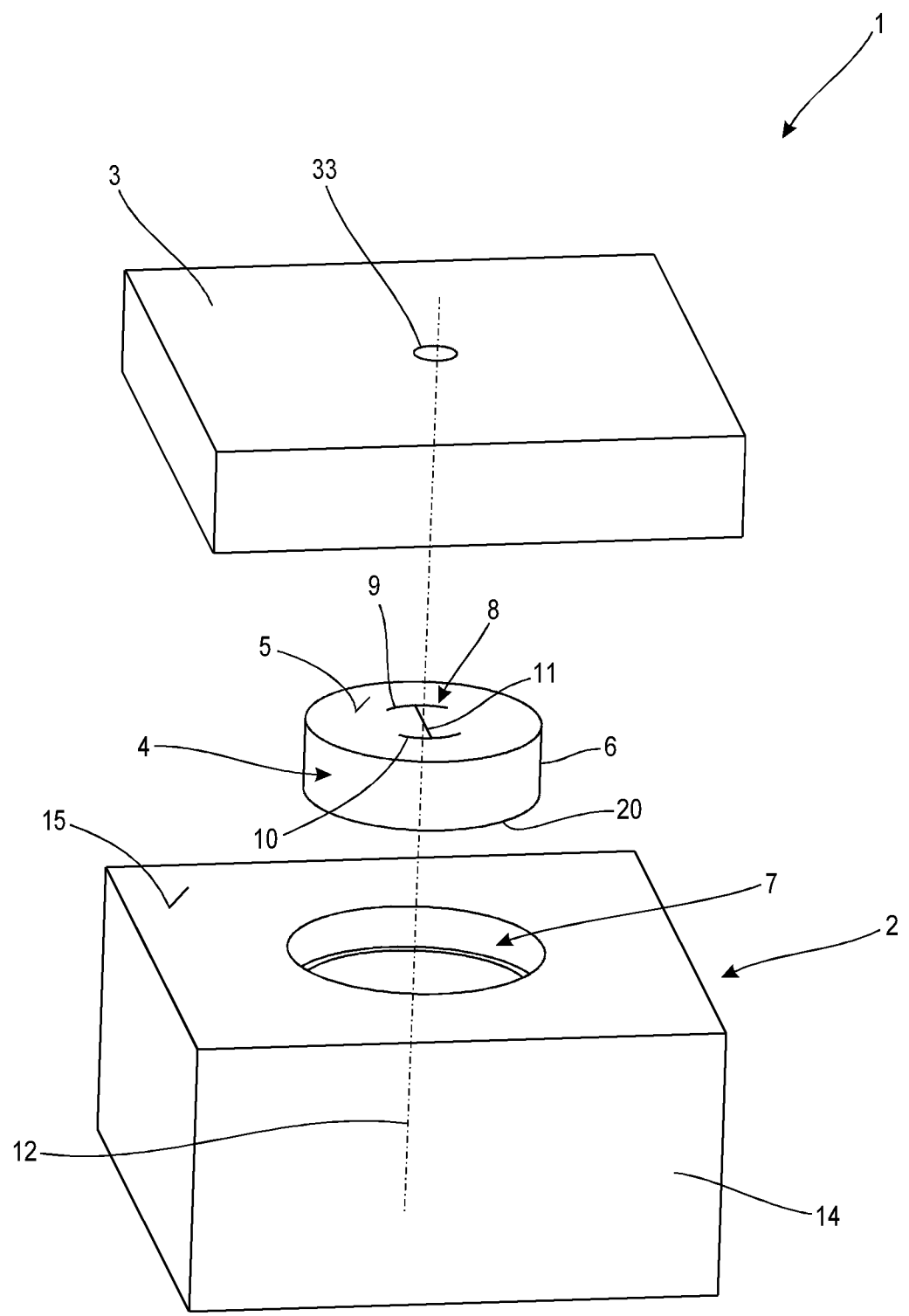

which is made of a resilient material and through which a fluid gap passes (8) that is designed such that the membrane seal (4), when in a resting position, seals the channel opening (18) and, when in an operative position, opens the channel opening (18), wherein at least one yielding depression (29) is formed in the coupling recess (7) adjacently to the channel opening (18), which depression is designed for an yielding movement of a region (36, 37) of the membrane seal (4) when the membrane seal (4) transitions from the resting position into the operative position.

14 Claims, 4 Drawing Sheets

(51) Int. Cl.
    *A61M 39/10*     (2006.01)
    *A61M 39/00*     (2006.01)
    *A61M 39/24*     (2006.01)
    *F16L 37/38*     (2006.01)

(52) U.S. Cl.
    CPC ............... *A61M 2039/0072* (2013.01); *A61M 2039/064* (2013.01); *A61M 2039/2426* (2013.01); *F16L 37/38* (2013.01); *F16L 2201/40* (2013.01)

(56) References Cited

U.S. PATENT DOCUMENTS

| | | | |
|---|---|---|---|
| 2005/0171489 A1* | 8/2005 | Weaver | A61M 5/16881 604/247 |
| 2005/0256460 A1 | 11/2005 | Rome et al. | |
| 2013/0165868 A1 | 6/2013 | Isaacson et al. | |
| 2014/0276462 A1* | 9/2014 | Vincent | A61M 39/0606 604/256 |

* cited by examiner

COUPLING COMPONENT AND FLUID COUPLING

This application is a National Stage Application of PCT/EP2017/083183, filed Dec. 17, 2017, which claims priority to German Patent Application No. 10 2016 015 205.2, filed Dec. 21, 2016.

The invention relates to a coupling component for a fluid coupling for releasably connecting fluid-conveying components, in particular fluid-conveying components in medical equipment, the coupling components comprising a coupling housing (14) through which a fluid channel passes in regions and which is provided with a coupling recess that is sunken into a surface of the coupling housing, a channel opening of the fluid channel ending at an end face of the coupling recess. The invention also relates to a fluid coupling having a coupling component of this kind.

The prior art discloses a plurality of different fluid couplings that allow fluid-conveying components to be releasably connected. An example of a fluid coupling of this kind for releasably connecting fluid-conveying components in the field of medical technology is the Luer system, which is widely used in the medical field.

The object of the invention is to provide a coupling component and a fluid coupling that can advantageously be cleaned and in which contaminants are prevented from undesirably entering the fluid channel of the coupling component.

This object is achieved by the features of the independent claims for a coupling component of the type mentioned at the outset. The dependent claims relate to advantageous embodiments of the invention.

In the coupling component according the invention, it is provided that the channel opening is covered by a membrane seal which is made of a resilient material and through which a fluid gap passes that is designed such that the membrane seal, when in a resting position, seals the channel opening and, when in an operative position, opens the channel opening, at least one yielding depression being formed in the coupling recess adjacently to the channel opening, which depression is designed for a yielding movement of a region of the membrane seal when the membrane seal transitions from the resting position into the operative position.

In this case, the membrane seal has a dual function since, when in the resting position, it seals the channel opening and, also in the resting position, additionally provides a surface within the coupling recess that is smooth and can therefore be cleaned effectively. Furthermore, the membrane seal and the coupling recess are matched to one another in such a way that the regions of the membrane seal that perform a yielding movement when said seal transitions from the resting position into the operative position on account of the elastic deformation that occurs during said transition can be brought into the operative position without, as far as possible, substantial mechanical resistance. This is in particular of interest if the coupling component is used together with a coupling device in order to form a fluid coupling. In this case, the coupling device is preferably designed to actively move the membrane seal out of the resting position into the operative position. In a fluid coupling of this kind, minimal fluid resistance to the fluid that flows in the fluid channel is thus ensured when the membrane seal is in the operative position, since the fluid itself must not elastically deform the membrane seal. Rather, this function is performed by the coupling device, which deforms the membrane seal at least in the region of the yielding depression and thus changes the shape of the fluid gap in its closed state of the resting position. Preferably, the membrane seal and the coupling recess are also matched to one another such that, when the coupling device is removed, the membrane seal resumes its original shape on account of its resilient properties. This ensures, without the influence of other external forces, that the resting position is resumed and thus that the channel opening is closed and a surface that is smooth and can be cleaned effectively is provided. Here, the coupling recess made in the surface of the coupling housing is designed such that the membrane seal ends flush with the surface of the coupling housing. Preferably, a sunken arrangement of the membrane seal is provided since improved protection against mechanical influences and resultant damage to the membrane seal can thus be ensured.

A preferred embodiment of the coupling component provides that the fluid gap extends prismatically between an upper side of the membrane seal facing away from the channel opening and a lower side of the membrane seal facing the channel opening. In a prismatic embodiment of the fluid gap, said gap always has a constant cross section in cross-sectional planes that are parallel to one another and oriented transversely to a space between the upper side and the lower side. Preferably, the fluid gap is made in the membrane seal, which is preferably formed in one piece, using a cutting method without removing material. A cutting method of this kind may, for example, be carried out using a knife or a cutting punch, only a minimal amount of material, preferably none, being removed when producing the fluid gap on account of a suitable shape and movement of the relevant cutting tool. As a result of this measure, the membrane seal has advantageous sealing properties when in the resting position. These sealing properties may also optionally be enhanced by the membrane seal being radially inwardly compressed in spatial directions transverse to the space between the upper side and the lower side such that opposing compression forces act on opposing wall portions of the fluid gap.

In a preferred embodiment, the fluid gap has a strain-relieving geometry on the edges thereof, in particular an H-shaped profiling. In order to prevent cracks from forming on the edges of the fluid gap, a strain-relieving geometry is intended to be provided on the opposing edge regions of the fluid gap, by means of which geometry internal tensions in the membrane seal can advantageously be distributed and thus reduced. By way of example, the fluid gap can be provided with holes in the edges thereof, the diameter of which holes is very small so as not to compromise the sealing effect of the membrane seal. Particularly preferably, it is provided that the fluid gap has an H-shaped profiling By said fluid gap being designed in such a manner, the two lateral legs of the H-shaped profiling of the fluid gap ensure relative mobility of predetermined regions of the membrane seal. During relative movement of said predetermined regions of the membrane seal between the resting position and the operative position, a gap cross section is widened for a region of the fluid gap, starting from zero up to a maximum cross section, as a result of which a fluid gap region that connects the two legs is spread open in the operative position, and thus allows fluid to flow through the membrane seal.

It is advantageous for the yielding depression to be formed in mirror symmetry or rotational symmetry with respect to a central axis of the channel opening. In conjunction with a positioning of the fluid gap over the channel opening that is as centric as possible and with a suitable coupling device for transferring the membrane seal from the resting position into the operative position, this allows the fluid gap to be opened at least substantially symmetrically and thus allows fluid to flow through the fluid gap at low friction. Preferably, it is provided that the yielding depression extends at least below end regions of the legs of the H-shaped profiling.

A particularly preferred embodiment provides that the membrane seal has a radially internal membrane region and a reinforcing portion that adjoins said region, is radially external, extends round the edge of said seal, in particular is annular, and is designed to fix the membrane seal in the coupling recess. Preferably, the internal membrane region is designed so as to be film-like or planar and to have a preferably constant material thickness, in particular designed as a plane-parallel region. Here, the material thickness of the membrane region is selected depending on the compression ratios that arise in the fluid channel and/or on the material properties of the membrane seal that is in particular made of a rubber-elastic material and/or on the cleaning power that arises when the coupling recess is being cleaned. By way of example, it is provided that the material thickness of the membrane region is in a range of from 5 percent to 25 percent of the distance between the two legs of the H-shaped profiling. Thereby, an advantageous compromise can be achieved between the deformation properties of the membrane seal and a fluid resistance caused by the membrane seal when fluid flows through the fluid channel. A circumferential reinforcing region radially externally adjoins the internal membrane region, which reinforcing region, firstly, is used to stabilise the membrane region and, secondly, can be used to fix the membrane seal in the coupling recess. Preferably, the reinforcing region is prismatic and extends in the same direction as the space between the upper side and the lower side of the membrane region, the reinforcing region being able to project beyond the upper side and/or lower side of the membrane region in said direction.

In an advantageous development of the invention, it is provided that a circumferential mounting channel for receiving the reinforcing portion at least in regions is formed in the coupling recess adjacently to the yielding depression, and that the reinforcing portion of the membrane seal is designed to be sealingly received in the mounting channel. By means of the mounting channel, a compact arrangement of the membrane seal in the coupling recess can be ensured.

It is expedient for the yielding depression and the mounting channel to each be designed as annular regions of the coupling recess that are coaxial with the channel opening. This ensures a simple mounting of the membrane seal in the coupling recess since care need not be taken to rotationally align the membrane seal with respect to the coupling recess.

The object of the invention is also achieved by a fluid coupling that comprises a coupling component according to any of the preceding claims and a coupling device, the coupling device being designed to be attached to the surface of the coupling housing and comprising a coupling projection that is designed to engage in the coupling recess, a fluid channel passing through the coupling projection, which coupling projection is designed to deflect a region of the membrane seal into the yielding depression. When the coupling device is attached to the coupling component, the coupling projection causes the membrane seal to be transferred from the resting position into the operative position, which is necessary for fluid to flow between the relevant fluid channels in an as undisturbed a manner as possible. This occurs on account of the mechanical influence of the coupling projection, which engages in the coupling recess when the coupling device is attached to the coupling component and thus deforms the membrane seal in regions. This brings about a pivot movement of regions of the membrane seal, said regions being able to yield into the yielding depression. Preferably, the forces transferred by the coupling device onto the membrane seal are within a predeterminable range that ensures in particular easy manual operation by a user at the same time as an adequate sealing effect for the fluid coupling. Here, a connection movement between the coupling device and the coupling component can be performed as a linear insertion movement or as a screwing movement in the form of a superimposition of a linear insertion movement on a rotational movement which occurs in particular about the central axis of the channel opening. The embodiment of the coupling device having the coupling projection is preferably selected such that, when the coupling device is attached to the coupling component, a continuous fluidically communicating connection between the two fluid channels is ensured independently of a fluid pressure in the fluid channels. When the coupling device is removed from the coupling component, the channel opening is automatically sealed on account of the resilient properties of the membrane seal, and therefore no further measures or technical devices are required for this purpose.

In a development of the fluid coupling, it is provided that the coupling projection is designed to extend circularly and to sealingly abut the membrane seal when in an operative position in order to ensure a communicating connection between the fluid channels in the coupling component and in the coupling device. In this development of the fluid coupling, it is advantageous that the membrane seal thus has a treble function such that, in addition to sealing the channel opening when in the resting position and ensuring a surface that is smooth and can be cleaned effectively, when in the resting position, it also provides the sealing between the two fluid channels of the coupling device and the coupling component. This sealing function is realised by the mechanical influence of the coupling projection on the membrane seal, by means of which projection the membrane seal is transferred from the resting position into the preferred position. This brings about a predeterminable axial compression of the membrane seal, which depends on the geometry of the membrane region and of the yielding recess and of the coupling projection and as a result of which existing gaps between the coupling projection and the coupling component are sealed.

Figure 2:
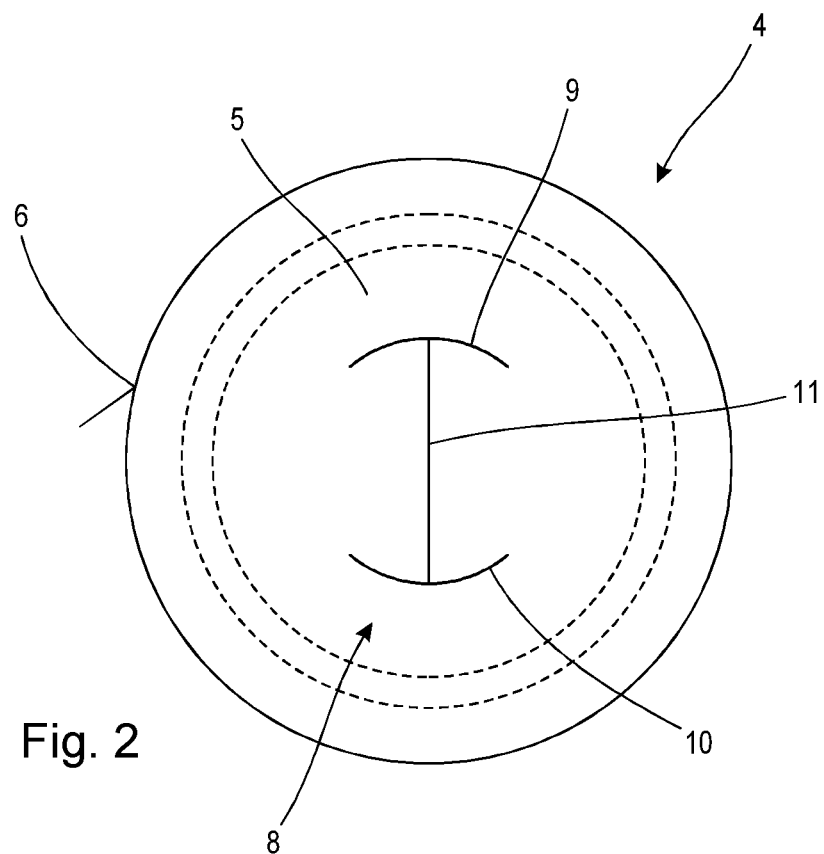
Figure 3:
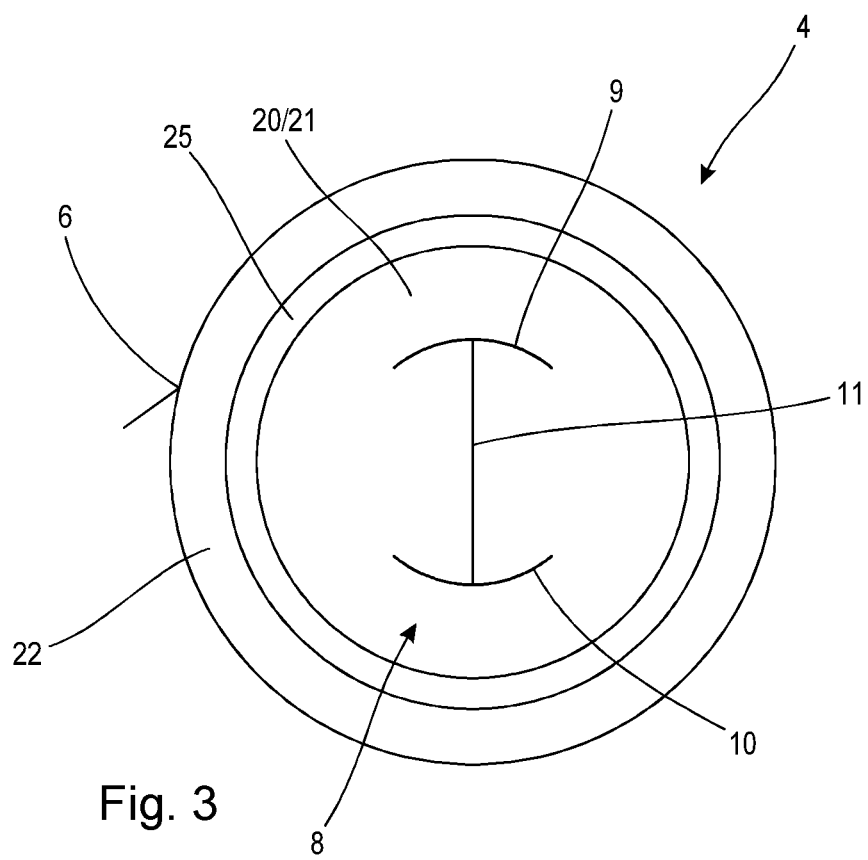
Figure 4:
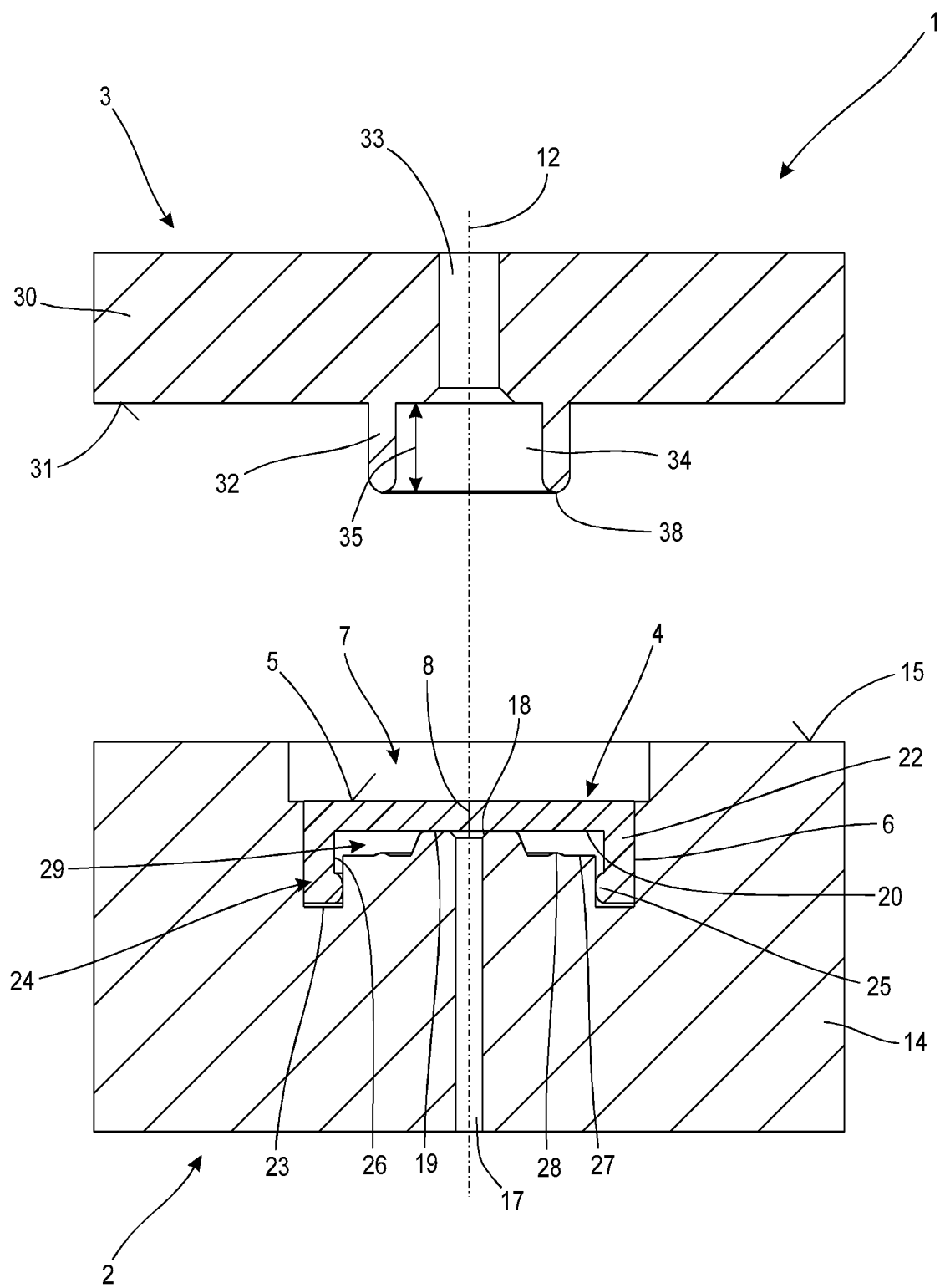
Figure 5:
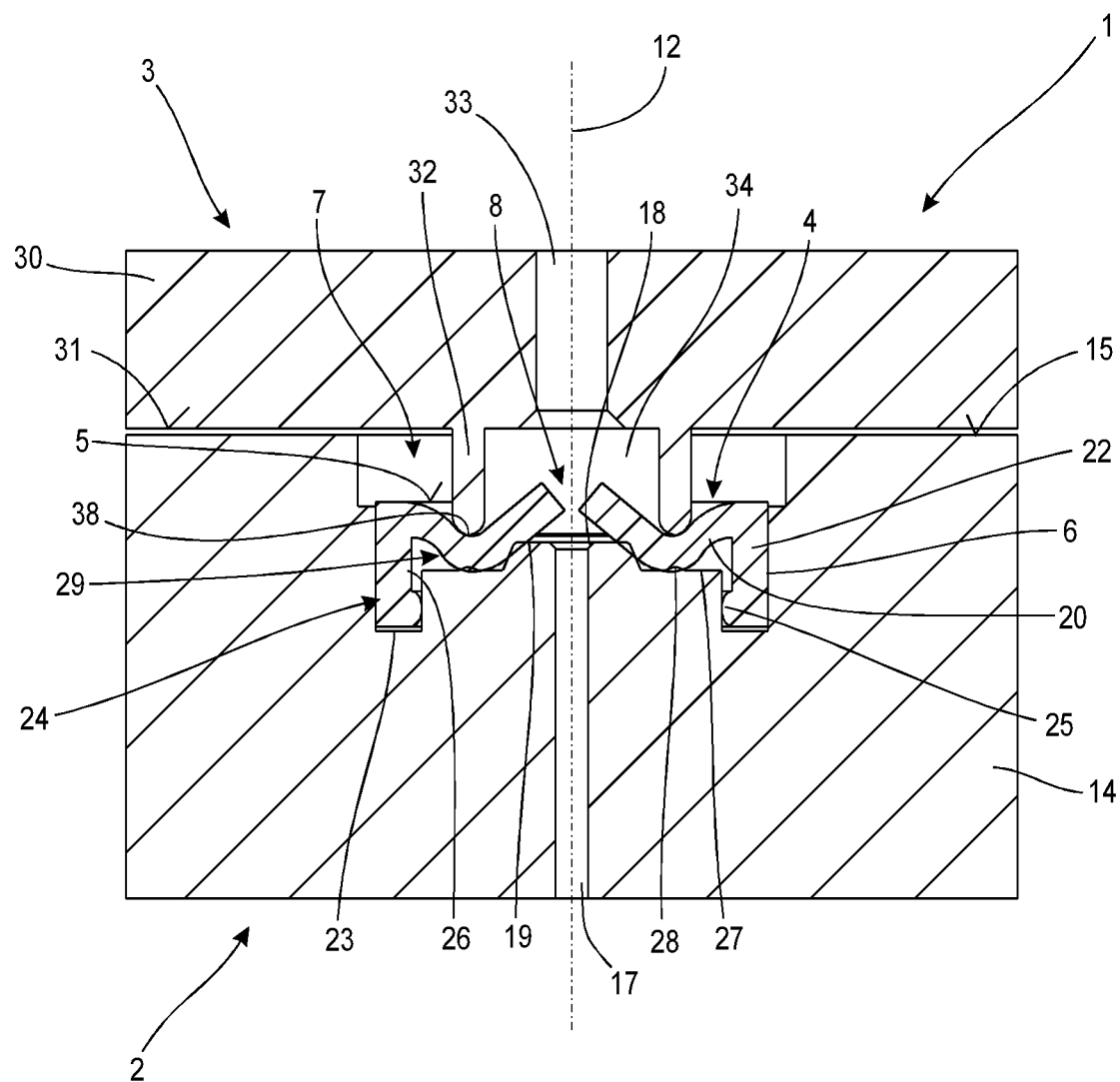

A preferred embodiment of the invention is shown in the drawings, in which:

FIG. 1 is a schematic, perspective view of a fluid coupling having a coupling component, a coupling device and a membrane seal provided for being mounted in the coupling component, FIG. 2 is a plan view of the membrane seal according to FIG. 1, FIG. 3 is a view from below of the membrane seal according to FIG. 1, FIG. 4 is a sectional view of the fluid coupling according to FIG. 1, the membrane seal being mounted in the coupling component and being in the resting position since the coupling device is arranged so as to be spaced apart from the coupling component, and FIG. 5 is a sectional view of the fluid coupling according to FIG. 1, the membrane seal being mounted in the coupling component and being in the operative position since the coupling device is attached to the coupling component.

A fluid coupling 1, shown purely schematically in FIG. 1, comprises a coupling component 2 and a coupling device 3. The coupling component 2 and the coupling device 3 are, for example, apparatuses (not shown in greater detail) that are intended to be fluidically coupled to one another by means of the fluid coupling. For example, the coupling component 2 may be designed as a component part of a fluid-conveying device, in particular a fluid pump, that is designed to provide a fluid from a storage tank (not shown). In this case, the coupling device 3 may, by way of example, be designed as a fluid consumer to which fluid can be supplied by the coupling component 2. The view in FIG. 1 shows a membrane seal 4 associated with the coupling component 2 in a dismounted position. It can therefore be seen that the membrane seal 4 has, by way of example, a circular surface 5 and an annular circumferential surface 6. As can be seen from FIGS. 4 and 5, which are described in greater detail below, the membrane seal 4 is mounted in a coupling recess 7 in the coupling component 2 in order to be able to perform the desired functions, which are described in greater detail below.

In the plan view according to FIG. 2 and in the view from below according to FIG. 3, the prismatic fluid gap 8, which has an H-shaped profiling, can be seen. By way of example, said gap is cut into the membrane seal 4 by means of a cutting punch (not shown) without a substantial amount of material thus being removed from the membrane seal 4. This ensures that, when the membrane seal is in the resting position, as shown in FIGS. 2 and 3, the fluid gap 8 does not have a free cross section that would allow fluid to pass through along the fluid gap 8. It is optionally enabled for fluid to flow through in such a manner by the membrane seal 4 being locally deformed or by the presence of a fluid pressure gradient above the membrane seal 4, which causes the material of the membrane seal 4 to elastically deform and thus the fluid gap 8 to open. By way of example, the prismatic fluid gap 8, which has an H-shaped profiling, comprises two legs 9, 10, which are each curved in the form of an arc and are interconnected by a connection line 11, the connection line 11 forming, by way of example, a perpendicular bisector for the two legs 9 and 10. Preferably, the fluid gap 8 has a constant profiling along a distance axis 12, shown in FIGS. 3 and 4, that is oriented perpendicularly to the plane of view of FIG. 2.

As can be seen from the view in FIGS. 4 and 5, a coupling recess 7 is made in a coupling housing 14 of the coupling component 2, starting from a surface 15, which recess is, purely by way of example, formed in rotational symmetry with respect to the distance axis 12. Furthermore, it is provided, by way of example, that the distance axis 12 is used as a central axis of a fluid channel 17 that is formed in the coupling component 2 and ends in a channel opening 18 at an end face 19 of the coupling recess 7. The end face 19 is annular and, by way of example, oriented in parallel with the surface 15. The membrane seal 4 is arranged in the coupling recess 7 such that, when in the resting position, as shown in FIG. 4, a lower side 20 of said seal abuts the end face 19 and seals the fluid channel 17 in a planar manner. The membrane seal 4 can be divided into a membrane region 21 which, purely by way of example, is circular and a radially external reinforcing region 22 that is integrally formed in one piece on the membrane region 21. Here, the membrane region 21 has a constant material thickness that is selected depending on the resilient properties and the expected compression ratios on the membrane seal 4 in order, for example, to always ensure reliable sealing of the fluid channel 17 in the absence of influence from the coupling device 3. The annular reinforcing portion 22 formed on the circumference is used to fix the membrane seal 4 in the coupling recess 7. For this purpose, an annular mounting channel 23 is formed on the circumference in the coupling recess 7 so as to be, purely by way of example, coaxial with the distance axis 12, into which channel an end region 24 of the reinforcing portion 22 can be mounted. In order to ensure sealing between the membrane seal 4 and the mounting channel 23, the end region 24 is provided, purely by way of example, with a sealing bulge 25 that faces radially inwards, is circumferential and is integrally formed in one piece.

The membrane seal 4 and the coupling recess 7 define a space that is used, at least in regions, for a yielding movement of the membrane seal 4 when said seal is transferred into the operative state, as shown in FIG. 5. This space is substantially delimited by the circular lower side 20 of the membrane seal 4, an annular inner surface 26 of the reinforcing portion 22 and an annular face 27 that is axially set back with respect to the end face 19. Purely by way of example, the annular face 27 is provided with a projection 28 that protrudes from the annular face 27 towards the surface 15 and is designed to promote the sealing effect between the membrane seal 4 and the coupling device 3.

Said space is also referred to as a yielding depression 29, since it allows for a yielding movement of regions of the membrane seal 4 when the coupling device 3 is mounted onto the coupling component 2.

The coupling device 3, which is shown purely schematically in FIGS. 4 and 5, comprises a main body 30 that has a coupling face 31 which is geometrically complementary to the surface 15 and is designed to abut the surface 15 in a planar manner. An annular coupling projection 32 protrudes from the coupling face 31, and the diameter of said projection corresponds, purely by way of example, to the diameter of the projection 28 in the coupling recess 7. Furthermore, a fluid channel 33 passes through the main body 30 and ends at an inner region 34 of the coupling projection 32. An axial extension 35 of the coupling projection 32 along the distance axis 12 is selected such that, when the coupling face 31 abuts the surface 15 in a planar manner, the coupling projection 32 can deform the membrane seal 4 in regions and move it into the yielding depression 29 in regions. During this displacement movement, which can also be considered as a transfer of the membrane seal 4 from the resting state into the operative state, membrane regions 36, 37 arranged between the legs 9, 10 of the fluid gap 8 are deformed in a curved manner, as shown in FIG. 5. Thus, the fluid gap 8 is spread open in the region of the connection line 11 and frees a fluid cross section, which allows for a fluidically communicating connection between the fluid channel 17 and the fluid channel 33.

Provided that the axial extension 35 of the coupling projection 32 is suitably configured, when the coupling device 3 is mounted on the coupling component 2, an annular end face 38 and the membrane seal 4 are made to abut the membrane seal 4 and the projection 28, respectively, all the way round, in addition to the membrane regions 36, 37 being deformed in a curved manner, and therefore complete fluidic sealing for a fluid channel system formed of the two fluid channels 17 and 33 is ensured. In addition to sealing the channel opening 18 when the membrane seal is in the resting state, and providing a surface of the coupling recess 7 that can be cleaned effectively when the membrane seal 4 is in the resting state, this constitutes an additional function of the membrane seal 4 when the coupling component 2 interacts with the coupling device 3.

The invention claimed is:

1. A coupling component for a fluid coupling for releasably connecting fluid-conveying components, the coupling component comprising:
   a coupling housing through which a fluid channel passes in regions, wherein a coupling recess is sunken into a surface of the coupling housing and a channel opening of the fluid ends at an end face of the coupling recess; and
   a membrane seal that covers the channel opening, the membrane seal being made of a resilient material and through which a fluid gap passes that is designed such that the membrane seal, when in a resting position, seals the channel opening, and, when in an operative position, opens the channel opening, wherein
   at least one yielding depression is formed in the coupling recess adjacently to the channel opening, the at least one yielding depression having a depth and being designed for a yielding movement of a region of the membrane seal when the membrane seal transitions from the resting position into the operative position,
   the membrane seal has a radially internal membrane region and a reinforcing portion that adjoins the radially internal membrane region, the reinforcing portion being radially external to the radially internal membrane and extending along an edge of the membrane seal, and
   a circumferential mounting channel is formed in the coupling recess surrounding the at least one yielding depression, the circumferential mounting channel having a depth greater than the depth of the at least one yielding depression within the coupling recess, and the reinforcing portion of the membrane seal is sealingly received in the circumferential mounting channel in the resting position and in the operative position.

2. The coupling component according to claim 1, wherein the fluid gap extends prismatically between an upper side of the membrane seal that faces away from the channel opening, and a lower side of the membrane seal that faces the channel opening, such that the fluid gap has a constant cross section in cross-sectional planes that are parallel to one another and oriented transversely to a space between the upper side and the lower side.

3. The coupling component according to claim 1, wherein the fluid gap has a strain-relieving geometry on edges thereof.

4. The coupling component according to claim 3, wherein the strain-relieving geometry on the edges of the fluid gap comprises H-shaped profiling.

5. The coupling component according to claim 1, wherein the at least one yielding depression is formed in mirror symmetry or rotational symmetry with respect to a central axis of the channel opening.

6. The coupling component according to claim 1, wherein the at least one yielding depression and the circumferential mounting channel are each designed as annular regions of the coupling recess, which are coaxial with the channel opening.

7. A fluid coupling for releasably connecting fluid-conveying components, comprising the coupling component according to claim 1 and a coupling device, the coupling device being designed to be attached to the surface of the coupling housing and comprising a coupling projection that is designed to engage in the coupling recess, wherein a fluid channel passes through the coupling projection and the coupling projection is designed to deflect a region of the membrane seal into the at least one yielding depression.

8. The fluid coupling according to claim 7, wherein the coupling projection is designed to extend circularly and to sealingly abut the membrane seal when in an operative position in order to ensure a communicating connection between the fluid channels in the coupling component and in the coupling device.

9. The fluid coupling according to claim 8, wherein the coupling projection, the membrane seal, and the at least one yielding depression are designed such that the coupling projection is sealed with respect to the membrane seal when in an operative position, and the membrane seal is sealed with respect to an abutment surface in the at least one yielding depression.

10. The fluid coupling according to claim 9, wherein the abutment surface in the at least one yielding depression is an annular face.

11. The fluid coupling according to claim 8, wherein the coupling projection has an annular end face.

12. The fluid coupling according to claim 7, wherein the fluid-conveying components are fluid-conveying components in medical equipment.

13. The coupling component according to claim 1, wherein the connecting fluid-conveying components are fluid-conveying components in medical equipment.

14. The coupling component according to claim 1, wherein the membrane seal is annular.

* * * * *